(12) United States Patent
Yamamoto

(10) Patent No.: US 11,169,369 B2
(45) Date of Patent: Nov. 9, 2021

(54) OBJECTIVE OPTICAL SYSTEM FOR ENDOSCOPE AND ENDOSCOPE

(71) Applicant: FUJIFILM Corporation, Tokyo (JP)

(72) Inventor: Chikara Yamamoto, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 355 days.

(21) Appl. No.: 16/135,041

(22) Filed: Sep. 19, 2018

(65) Prior Publication Data
US 2019/0094515 A1   Mar. 28, 2019

(30) Foreign Application Priority Data

Sep. 27, 2017   (JP) .............................. JP2017-187093

(51) Int. Cl.
G02B 23/24 (2006.01)
A61B 1/00 (2006.01)
G02B 13/04 (2006.01)

(52) U.S. Cl.
CPC ........ G02B 23/243 (2013.01); A61B 1/00096 (2013.01); G02B 13/04 (2013.01); G02B 23/2461 (2013.01)

(58) Field of Classification Search
CPC .................................. G02B 23/2407–23/2438
USPC ................................................. 359/656–661
See application file for complete search history.

(56) References Cited

U.S. PATENT DOCUMENTS 2,519,760 A * 8/1950 Hett .................... G02B 23/2407
  359/367
3,825,315 A * 7/1974 Altman ................ G02B 15/173
  250/349
4,764,001 A   8/1988 Yokota
4,806,001 A   2/1989 Okabe et al.
4,867,549 A   9/1989 Sekine
5,233,473 A   8/1993 Kanamori
5,633,754 A * 5/1997 Hoogland .......... G02B 13/0095
  359/434
5,833,596 A * 11/1998 Bonnell ................... A61B 5/01
  600/109

(Continued)

FOREIGN PATENT DOCUMENTS

CN          1953698 A    4/2007
CN        101479642 A    7/2009

(Continued)

OTHER PUBLICATIONS

Zavjalov; RU 2581435 C1 with human translation; Apr. 2016 (Year: 2016).*

(Continued)

*Primary Examiner* — Zachary W Wilkes

(74) *Attorney, Agent, or Firm* — Sughrue Mion, PLLC

(57) ABSTRACT

An objective optical system for an endoscope forms an intermediate image at a position conjugate to an object surface, forms the intermediate image on an imaging plane again, and includes an aperture stop that is provided between the intermediate image and the imaging plane. Conditional expression (1) is satisfied in a case in which a distance between a lens surface closest to an object and a paraxial entrance pupil position on an optical axis is denoted by FS and a focal length of the entire system is denoted by f, $$|FS/f|<0.75 \qquad (1)$$

14 Claims, 17 Drawing Sheets

EXAMPLE 1

(56) References Cited

U.S. PATENT DOCUMENTS

| | | | | |
|---|---|---|---|---|
| 6,052,234 | A * | 4/2000 | Mukai | G02B 23/14 |
| | | | | 359/558 |
| 6,075,646 | A | 6/2000 | Suzuki | |
| 6,545,802 | B2 * | 4/2003 | Hoogland | G02B 13/0095 |
| | | | | 359/362 |
| 7,230,756 | B2 * | 6/2007 | Hoogland | G02B 23/243 |
| | | | | 359/362 |
| 9,565,996 | B2 * | 2/2017 | Berkner | A61B 1/00186 |
| 2007/0055100 | A1 | 3/2007 | Kato et al. | |
| 2009/0052062 | A1 | 2/2009 | Fujiwara | |
| 2009/0256949 | A1 | 10/2009 | Rana | |
| 2015/0234157 | A1 | 8/2015 | Ichimura | |
| 2016/0178884 | A1 | 6/2016 | Hanada et al. | |
| 2016/0238831 | A1 | 8/2016 | Baba | |
| 2017/0119237 | A1 | 5/2017 | Bedard et al. | |
| 2017/0131537 | A1 | 5/2017 | Duckett, III | |
| 2019/0200847 | A1 * | 7/2019 | Uchida | G02B 23/26 |

FOREIGN PATENT DOCUMENTS

| | | | | |
|---|---|---|---|---|
| CN | 105717627 | A | 6/2016 | |
| CN | 106802479 | A | 6/2017 | |
| JP | 62-173415 | A | 7/1987 | |
| JP | S63276012 | A | 11/1988 | |
| JP | H04146405 | A | 5/1992 | |
| JP | H08190056 | A | 7/1996 | |
| JP | H10509812 | A | 9/1998 | |
| JP | 5185578 | B2 | 4/2013 | |
| JP | 2015152764 | A | 8/2015 | |
| JP | 2016-151629 | A | 8/2016 | |
| JP | 2017086900 | A | 5/2017 | |
| RU | 2581435 | C1 * | 4/2016 | G02B 23/24 |

OTHER PUBLICATIONS

Communication dated Aug. 18, 2020, from the Japanese Patent Office in Application No. 2017-187093.

Notice of Reasons for Refusal dated Feb. 9, 2021 from the Japanese Patent Office in JP Application No. 2017-187093.

Communication dated Jun. 18, 2021, issued by the State Intellectual Property Office of the P.R.C. in application No. 201811121349.5.

* cited by examiner

EXAMPLE 1

EXAMPLE 2

EXAMPLE 3

EXAMPLE 5

EXAMPLE 6

EXAMPLE 8

EXAMPLE 2

EXAMPLE 3

EXAMPLE 5

EXAMPLE 6

EXAMPLE 7

OBJECTIVE OPTICAL SYSTEM FOR ENDOSCOPE AND ENDOSCOPE

CROSS REFERENCE TO RELATED APPLICATIONS

The present application claims priority under 35 U.S.C. § 119 to Japanese Patent Application No. 2017-187093 filed on Sep. 27, 2017. The above application is hereby expressly incorporated by reference, in its entirety, into the present application.

BACKGROUND OF THE INVENTION

1. Field of the Invention

The present invention relates to an objective optical system for an endoscope and an endoscope including the objective optical system for an endoscope.

2. Description of the Related Art

In the past, an insertable endoscope, which includes an imaging device built in a distal end portion of a long insertion part thereof and images the inside of a body cavity in a state in which the long insertion part is inserted into the body cavity through a mouth, a nose, or the like of an examinee, has been widespread in a medical field. For example, objective optical systems disclosed in JP2016-151629A and JP5185578B are known as objective optical systems that can be used for such an endoscope.

SUMMARY OF THE INVENTION

Since the above-mentioned endoscopes tend to increase in the number of pixels and the angle of view and images obtained through close-up imaging have been taken in and have been subjected to detailed analysis and observation, it is desirable that image quality is further improved. Further, for the simplification of a countermeasure for a sterilization treatment for preventing an infection and a repair countermeasure, the number of cases in which a cover glass is disposed on the side of an objective optical system closest to an object has also increased.

The objective optical system disclosed in JP2016-151629A is known as an objective optical system that copes with an increase in the number of pixels and the angle of view. To cope with an increase in the number of pixels, this objective optical system is provided with three lenses disposed to be closer to an object than a stop and three lenses disposed to be closer to an image than the stop and this objective optical system corrects the aberration of a wide angle area at a position where the height of a ray in the wide angle area is increased. However, since the effective luminous flux diameter on a lens surface closest to the object is increased, there is a problem that the diameter of a lens close to the object is increased.

In a case in which the lens close to the object is increased in size, the disposition of an illumination light distribution-optical system to be disposed near the objective optical system is limited. For this reason, the objective optical system and the illumination light distribution-optical system cannot be disposed close to each other. As a result, since illumination light in a proximity area particularly has a distribution, detailed analysis or observation is affected. Further, in a case in which the cover glass is to be disposed on the side of the objective optical system closest to an object, the diameter of a cover glass would be very large and this is contrary to a demand for reduction in the size of the endoscope.

The objective optical system disclosed in JP5185578B is known as an objective optical system that copes with a reduction in diameter. This objective optical system is an optical system of which the diameter is reduced through the formation of an intermediate image in an optical system, but cannot be used as an objective optical system for an endoscope since the angle of view thereof is narrow.

The invention has been made in consideration of the above-mentioned circumstances, and an object of the invention is to provide an objective optical system for an endoscope that has a wide angle, a small effective luminous flux diameter on a lens surface closest to an object, and good optical performance, and an endoscope including the objective optical system for an endoscope.

An objective optical system for an endoscope of the invention forms an intermediate image at a position conjugate to an object surface, forms the intermediate image on an imaging plane again, and comprises a stop provided between the intermediate image and the imaging plane. Conditional expression (1) is satisfied in a case in which a distance between a lens surface closest to an object and a paraxial entrance pupil position on an optical axis is denoted by FS and a focal length of the entire system is denoted by f.

$$|FS/f| < 0.75 \tag{1}$$

It is preferable that Conditional expression (1-1) is satisfied.

$$0 \le |FS/f| < 0.5 \tag{1-1}$$

In the objective optical system for an endoscope of the invention, in a case in which a paraxial relay magnification of the intermediate image on the imaging plane is denoted by $\beta R$, it is preferable that Conditional expression (2) is satisfied and it is more preferable that Conditional expression (2-1) is satisfied.

$$-2 < \beta R < -0.8 \tag{2}$$

$$-1.5 < \beta R < -0.9 \tag{2-1}$$

In a case in which the height of the intermediate image is denoted by HM and an image height on the imaging plane is denoted by HI as shown in FIG. 18, the relay magnification $\beta R$ is expressed by the following equation.

$$\beta R = HI/HM$$

Further, in a case in which a maximum effective luminous flux diameter among effective luminous flux diameters on lens surfaces of the entire system is denoted by BD and a maximum effective image height on the imaging plane is denoted by HI, it is preferable that Conditional expression (3) is satisfied and it is more preferable that Conditional expression (3-1) is satisfied.

$$BD/(2 \times HI) < 1.2 \tag{3}$$

$$0.5 < BD/(2 \times HI) < 1.1 \tag{3-1}$$

Further, in a case in which the maximum effective image height on the imaging plane is denoted by HI, a half angle of view of the entire system is denoted by ω, and the focal length of the entire system is denoted by f, it is preferable that Conditional expression (4) is satisfied and it is more preferable that Conditional expression (4-1) is satisfied.

$$HI/(\tan(\omega) \times |f|) < 0.75 \tag{4}$$

$$0.01 < HI/(\tan(\omega) \times |f|) < 0.65 \tag{4-1}$$

Furthermore, it is preferable that the objective optical system for an endoscope further comprises a plane-parallel plate provided to be closer to the object than the lens surface closest to the object.

An endoscope of the invention comprises the above-mentioned objective optical system for an endoscope of the invention.

An objective optical system for an endoscope of the invention forms an intermediate image at a position conjugate to an object surface, forms the intermediate image on an imaging plane again, and includes a stop provided between the intermediate image and the imaging plane. Conditional expression (1) is satisfied in a case in which a distance between a lens surface closest to an object and a paraxial entrance pupil position on an optical axis is denoted by FS and a focal length of the entire system is denoted by f. Accordingly, it is possible to provide an objective optical system for an endoscope that has a wide angle, a small effective luminous flux diameter on a lens surface closest to an object, and good optical performance, and an endoscope including the objective optical system for an endoscope.

$$|FS/f|<0.75 \qquad (1)$$

DESCRIPTION OF THE PREFERRED EMBODIMENTS

Figure 1:
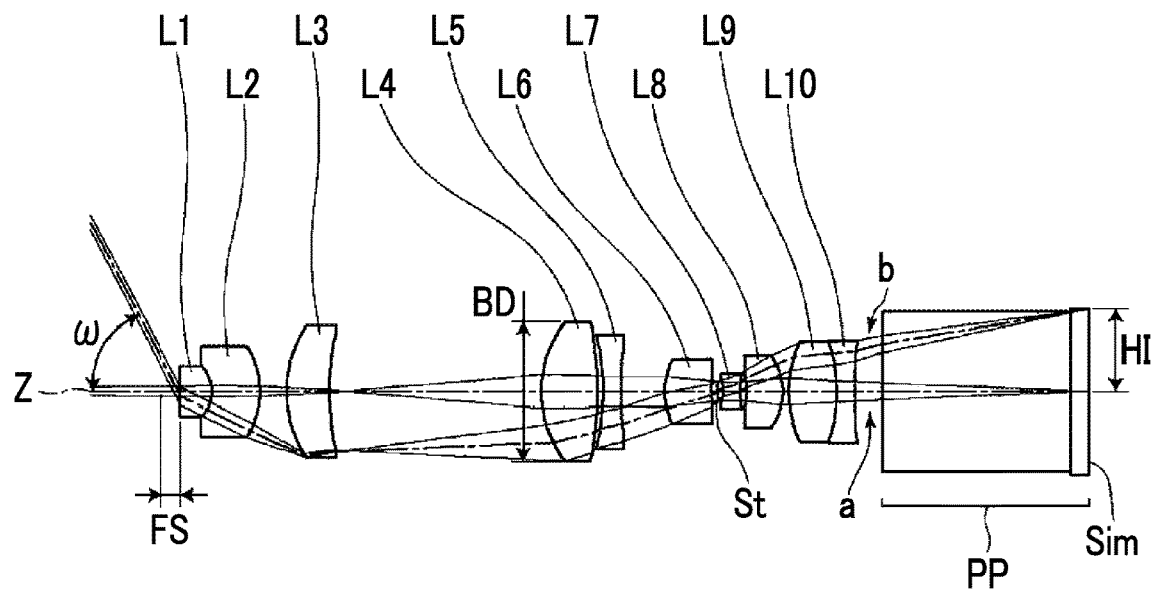
FIG. 1 is a cross-sectional view showing the structure (common to Example 1) of an objective optical system for an endoscope according to an embodiment of the invention.

An embodiment of the invention will be described in detail below with reference to the drawings. FIG. 1 is a cross-sectional view showing the structure of an objective optical system for an endoscope according to an embodiment of the invention. A structure example shown in FIG. 1 is common to the structure of an objective optical system for an endoscope of Example 1 to be described later. In FIG. 1, a left side is an object side, a right side is an image side, and an aperture stop St shown FIG. 1 does not necessarily represent a size or a shape and represents the position on an optical axis Z. Further, in FIG. 1, luminous flux a on an axis, luminous flux b corresponding to the maximum angle of view, and the like are shown together with symbols of the respective conditional expressions.

FIG. 1 shows an example in which an optical member PP, of which an incident surface and an emitting surface are parallel to each other, is disposed between the objective optical system for an endoscope and an imaging plane Sim. The optical member PP is assumed as an optical path-converting prism that is used to bend an optical path, a filter, and/or a cover glass, and the optical member PP may be omitted in the invention. A bent optical path is formed in a case in which an optical path-converting prism is used, but a drawing in which an optical path is not bent is shown in FIG. 1 for easy understanding.

The objective optical system for an endoscope of this embodiment forms an intermediate image at a position conjugate to an object surface and forms the intermediate image on the imaging plane Sim again, includes an aperture stop St provided between the intermediate image and the imaging plane Sim, and is adapted to satisfy Conditional expression (1) in a case in which a distance between a lens surface closest to an object and a paraxial entrance pupil position on the optical axis is denoted by FS and the focal length of the entire system is denoted by f.

$$|FS/f|<0.75 \qquad (1)$$

Since the intermediate image is formed in the objective optical system for an endoscope, the diameter of a lens can be reduced while an aberration in an increase in the angle of view is corrected. Further, since the aperture stop St is provided between the intermediate image and the imaging plane Sim, a reduction in the amount of ambient light caused by the thickness of the aperture stop St can be suppressed in comparison with that in a case in which the aperture stop St is provided to be closer to the object than the intermediate image.

Since it is possible to prevent the diameter of a front lens from being excessively increased by making |FS/f| smaller than the upper limit of Conditional expression (1), it is advantageous in ensuring a space in which an illumination optical system is disposed and/or disposing a plane-parallel plate, such as a cover glass. Better characteristics can be obtained in a case in which Conditional expression (1-1) is satisfied.

$$0 \leq |FS/f| < 0.5 \quad (1\text{-}1)$$

It is preferable that Conditional expression (2) is satisfied in objective optical system for an endoscope of this embodiment in a case in which a paraxial relay magnification of the intermediate image on the imaging plane is denoted by βR. Since it is possible to prevent an aberration caused by a lens, which is closer to the object than the intermediate image, from being excessively increased on the imaging plane Sim by making βR larger than the lower limit of Conditional expression (2), it is advantageous in correcting an aberration. It is possible to prevent an increase in the diameter of a lens, which is provided near the intermediate image, by making βR smaller than the upper limit of Conditional expression (2). Better characteristics can be obtained in a case in which Conditional expression (2-1) is satisfied.

$$-2 < \beta R < -0.8 \quad (2)$$

$$-1.5 < \beta R < -0.9 \quad (2\text{-}1)$$

Further, it is preferable that Conditional expression (3) is satisfied in a case in which the maximum effective luminous flux diameter among the effective luminous flux diameters on the respective lens surfaces of the entire system is denoted by BD and the maximum effective image height on the imaging plane Sim is denoted by HI. Since it is possible to prevent the diameter of a lens from being excessively increased by making BD/(2×HI) smaller than the upper limit of Conditional expression (3), it is advantageous in reducing the size of an insertion part of an endoscope. Better characteristics can be obtained in a case in which Conditional expression (3-1) is satisfied. In a case in which BD/(2×HI) is made larger than the lower limit of Conditional expression (3-1), it is advantageous in correcting astigmatism and distortion.

$$BD/(2 \times HI) < 1.2 \quad (3)$$

$$0.5 < BD/(2 \times HI) < 1.1 \quad (3\text{-}1)$$

Furthermore, it is preferable that Conditional expression (4) is satisfied in a case in which the maximum effective image height on the imaging plane Sim is denoted by HI, the half angle of view of the entire system is denoted by ω, and the focal length of the entire system is denoted by f. It is possible to prevent an image of a portion, which is to be observed in detail and positioned near an optical axis, from being excessively reduced in size and to ensure the amount of light at a peripheral portion by making HI/(tan(ω)×|f|) smaller than the upper limit of Conditional expression (4). Better characteristics can be obtained in a case in which Conditional expression (4-1) is satisfied. Since it is possible to prevent the angle of view from being excessively increased by making HI/(tan(ω)×|f|) larger than the lower limit of Conditional expression (4-1), it is possible to prevent the lack of the amount of illumination light to be applied to an object to be observed.

$$HI/(\tan(\omega) \times |f|) < 0.75 \quad (4)$$

$$0.01 < HI/(\tan(\omega) \times |f|) < 0.65 \quad (4\text{-}1)$$

Further, it is preferable that a plane-parallel plate, such as a cover glass, is provided to be closer to the object than a lens surface closest to the object. In a case in which such a plane-parallel plate is provided, it is possible to simplify a countermeasure for a sterilization treatment for preventing an infection and a repair countermeasure.

Next, numerical examples of the objective optical system for an endoscope of the invention will be described. First, an objective optical system for an endoscope of Example 1 will be described. FIG. 1 is a cross-sectional view showing the structure of the objective optical system for an endoscope of Example 1. In FIG. 1 and FIGS. 2 to 8 corresponding to Examples 2 to 8 to be described later, a left side is an object side, a right side is an image side, and the aperture stop St shown FIG. 1 does not necessarily represent a size or a shape and represents the position on the optical axis Z. Further, in FIGS. 1 to 8, luminous flux a on an axis and luminous flux b corresponding to the maximum angle of view are shown together with each other.

The objective optical system for an endoscope of Example 1 includes 10 lenses, that is, lenses L1 to L10 in this order from the object, and has a structure in which the aperture stop St is disposed in the objective optical system for an endoscope.

The lens data of the objective optical system for an endoscope of Example 1 is shown in Table 1. Numerical values of the lens data are numerical values in a case in which the focal length f is standardized as 1. The meanings of symbols shown in Table 1 will be described in the following description using the objective optical system for an endoscope of Example 1 by way of example, but are basically the same as those of Examples 2 to 8.

In the lens data of Table 1, surface numbers, which are sequentially increased toward an image surface from the surface of a component closest to the object as a first surface, are shown in the column of a surface number, the curvature radii of the respective surfaces are shown in the column of a curvature radius, and a spacing between each surface and the next surface on the optical axis Z is shown in the column of a surface spacing. Further, the refractive indexes of the optical elements with respect to a d line (a wavelength of 587.6 nm (nanometer)) are shown in the column of n, Abbe's numbers of the respective optical elements with respect to a d line (a wavelength of 587.6 nm (nanometer)) are shown in the column of ν, and the effective luminous flux diameter on a lens surface closest to an object and the effective luminous flux diameter on a lens surface having the maximum effective luminous flux diameter are shown in the column of an effective luminous flux diameter. Further, the value of the maximum effective image height HI on the imaging plane Sim is shown together in the lens data.

The sign of a curvature radius is positive in a case in which the shape of a surface is convex toward the object, and is negative in a case in which the shape of a surface is convex toward the image surface. The object surface, the aperture stop St, the optical member PP, and the imaging plane Sim are also included and shown in the lens data, and a plane-parallel plate CP is also included and shown in the lens data in the case of an example including the plane-parallel plate CP. The expression of "(St)" is shown together with a surface number in the column of the surface number of a surface corresponding to the aperture stop St.

TABLE 1

Example 1•LENS DATA (n, ν ARE d LINE)

| Surface Number | Curvature Radius | Surface Spacing | n | ν | Effective Luminous Flux Diameter |
|---|---|---|---|---|---|
| Object Surface | ∞ | 7.850 | | | |
| 1 | ∞ | 0.416 | 2.00100 | 29.1 | 0.437 |
| 2 | −0.473 | 0.628 | 1.89286 | 20.4 | |
| 3 | −1.106 | 0.328 | | | |
| 4 | 1.541 | 0.559 | 2.00100 | 29.1 | |
| 5 | 3.395 | 2.785 | | | |
| 6 | 1.491 | 0.726 | 1.88300 | 40.8 | 1.811 |
| 7 | −4.662 | 0.079 | | | |
| 8 | −2.877 | 0.236 | 1.89286 | 20.4 | |
| 9 | 5.544 | 0.570 | | | |
| 10 | 0.937 | 0.616 | 1.89286 | 20.4 | |
| 11 | 3.675 | 0.079 | | | |
| 12(St) | ∞ | 0.063 | | | |
| 13 | −0.675 | 0.236 | 1.95906 | 17.5 | |
| 14 | 1.705 | 0.079 | | | |
| 15 | −1.295 | 0.478 | 1.83481 | 42.7 | |
| 16 | −0.783 | 0.079 | | | |
| 17 | 1.588 | 0.631 | 1.72916 | 54.7 | |
| 18 | −2.008 | 0.236 | 1.84666 | 23.8 | |
| 19 | 5.952 | 0.348 | | | |
| 20 | ∞ | 2.474 | 1.55920 | 53.9 | |
| 21 | ∞ | 0.236 | 1.51633 | 51.6 | |
| Imaging Plane | ∞ | 0.000 | | | |

HI = 1.079

Figure 9:
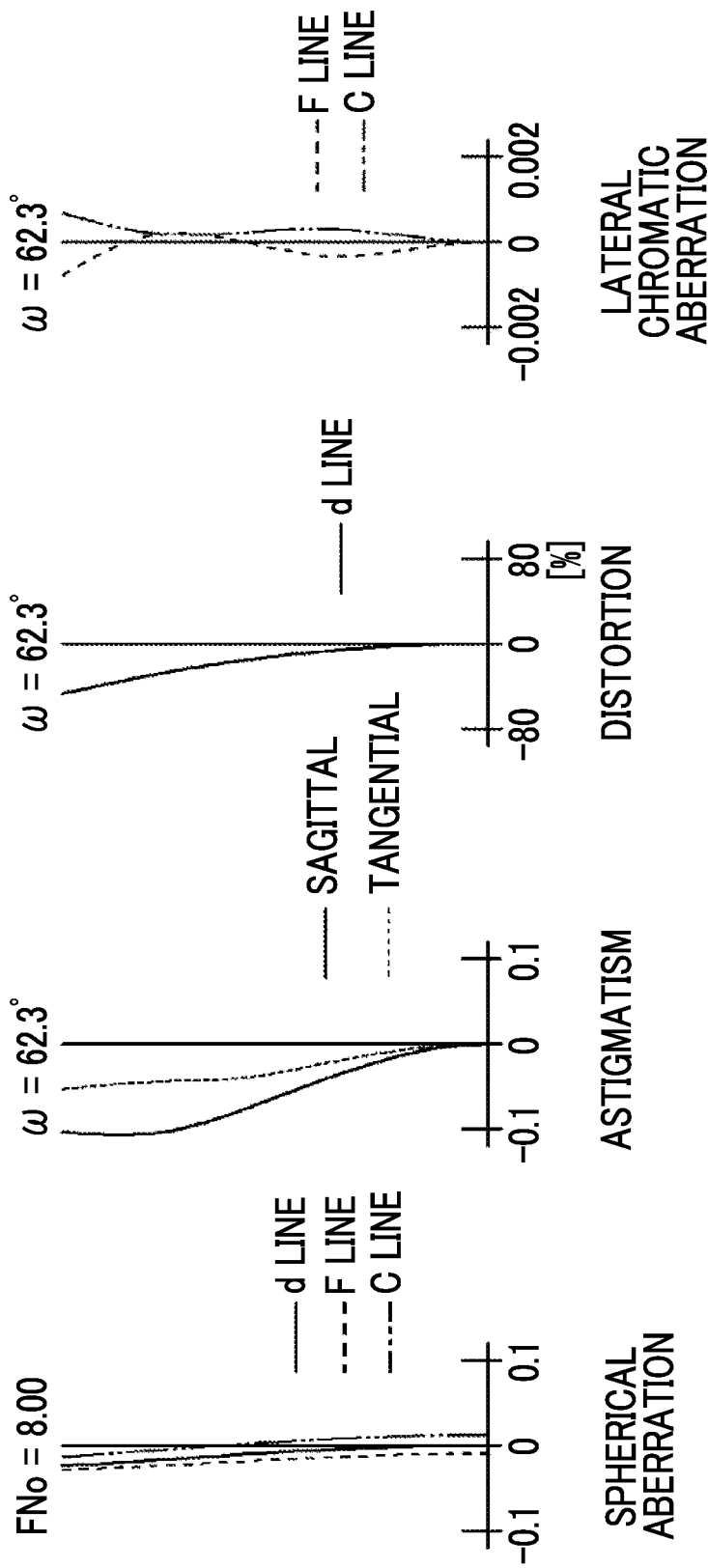
FIG. 9 is a diagram showing the respective aberrations of the objective optical system for an endoscope of Example 1 of the invention.

Diagrams showing the respective aberrations of the objective optical system for an endoscope of Example 1 are shown in FIG. 9. A spherical aberration, astigmatism, distortion, and a lateral chromatic aberration are shown in this order from the left side in FIG. 9. Aberrations, which are obtained in a case in which a d line (a wavelength of 587.6 nm (nanometer)) is used as a reference wavelength, are shown in the diagrams that show the spherical aberration, the astigmatism, and the distortion. In the diagram showing the spherical aberration, aberrations corresponding to a d line (a wavelength of 587.6 nm (nanometer)), an F line (a wavelength of 486.1 nm (nanometer)), and a C line (a wavelength of 656.3 nm (nanometer)) are shown by a solid line, a dotted line, and a two-dot chain line, respectively. In the diagram showing the astigmatism, aberrations in a sagittal direction and a tangential direction are shown by a solid line and a dotted line, respectively. In the diagram showing the lateral chromatic aberration, aberrations corresponding to an F line (a wavelength of 486.1 nm (nanometer)) and a C line (a wavelength of 656.3 nm (nanometer)) are shown by a dotted line and a two-dot chain line, respectively. FNo in the diagram showing the spherical aberration means an F-Number and ω in the diagrams showing the other aberrations means the half angle of view.

Figure 2:
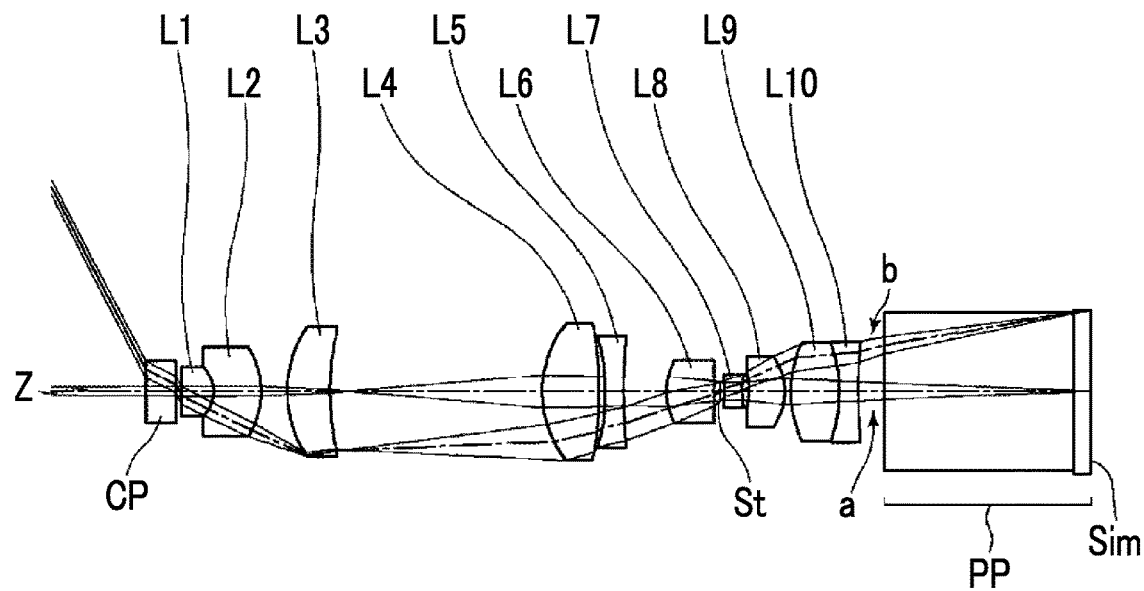
FIG. 2 is a cross-sectional view showing the structure of an objective optical system for an endoscope of Example 2 of the invention.
Figure 10:
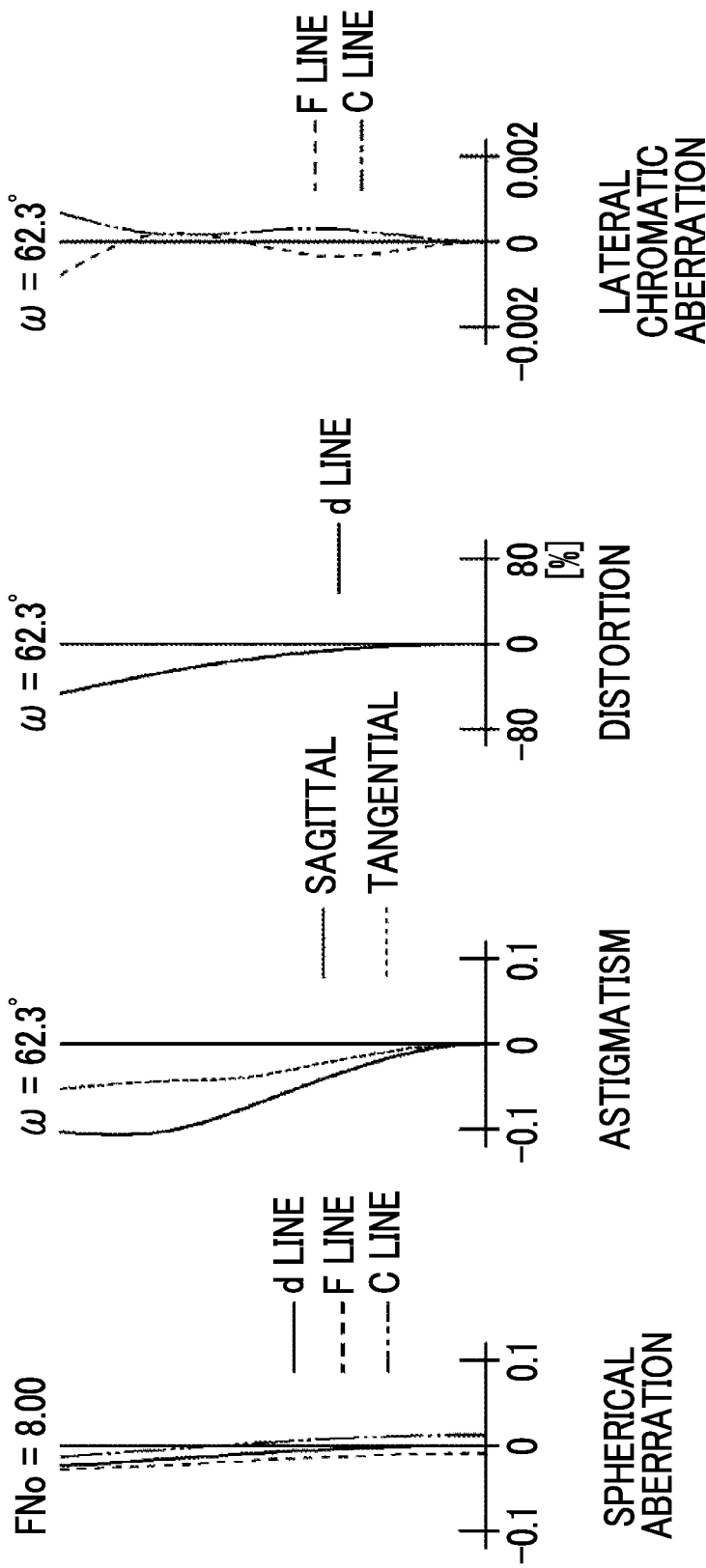
FIG. 10 is a diagram showing the respective aberrations of the objective optical system for an endoscope of Example 2 of the invention.

Next, an objective optical system for an endoscope of Example 2 will be described. FIG. 2 is a cross-sectional view showing the structure of the objective optical system for an endoscope of Example 2. The objective optical system for an endoscope of Example 2 includes a plane-parallel plate CP and 10 lenses, that is, lenses L1 to L10 in this order from an object, and has a structure in which an aperture stop St is disposed in the objective optical system for an endoscope. Further, the lens data of the objective optical system for an endoscope of Example 2 is shown in Table 2, and diagrams showing the respective aberrations of the objective optical system for an endoscope of Example 2 are shown in FIG. 10.

TABLE 2

Example 2•LENS DATA (n, ν ARE d LINE)

| Surface Number | Curvature Radius | Surface Spacing | n | ν | Effective Luminous Flux Diameter |
|---|---|---|---|---|---|
| Object Surface | ∞ | 7.850 | | | |
| 1 | ∞ | 0.393 | 1.88299 | 40.8 | |
| 2 | ∞ | 0.079 | | | |
| 3 | ∞ | 0.416 | 2.00100 | 29.1 | 0.437 |
| 4 | −0.473 | 0.628 | 1.89286 | 20.4 | |
| 5 | −1.106 | 0.328 | | | |
| 6 | 1.541 | 0.559 | 2.00100 | 29.1 | |
| 7 | 3.395 | 2.785 | | | |
| 8 | 1.491 | 0.726 | 1.88300 | 40.8 | 1.811 |
| 9 | −4.662 | 0.079 | | | |
| 10 | −2.877 | 0.236 | 1.89286 | 20.4 | |
| 11 | 5.544 | 0.570 | | | |
| 12 | 0.937 | 0.616 | 1.89286 | 20.4 | |
| 13 | 3.675 | 0.079 | | | |
| 14(St) | ∞ | 0.063 | | | |
| 15 | −0.675 | 0.236 | 1.95906 | 17.5 | |
| 16 | 1.705 | 0.079 | | | |
| 17 | −1.295 | 0.478 | 1.83481 | 42.7 | |
| 18 | −0.783 | 0.079 | | | |
| 19 | 1.588 | 0.631 | 1.72916 | 54.7 | |
| 20 | −2.008 | 0.236 | 1.84666 | 23.8 | |
| 21 | 5.952 | 0.348 | | | |
| 22 | ∞ | 2.474 | 1.55920 | 53.9 | |
| 23 | ∞ | 0.236 | 1.51633 | 51.6 | |
| Imaging Plane | ∞ | 0.000 | | | |

HI = 1.079

Figure 3:
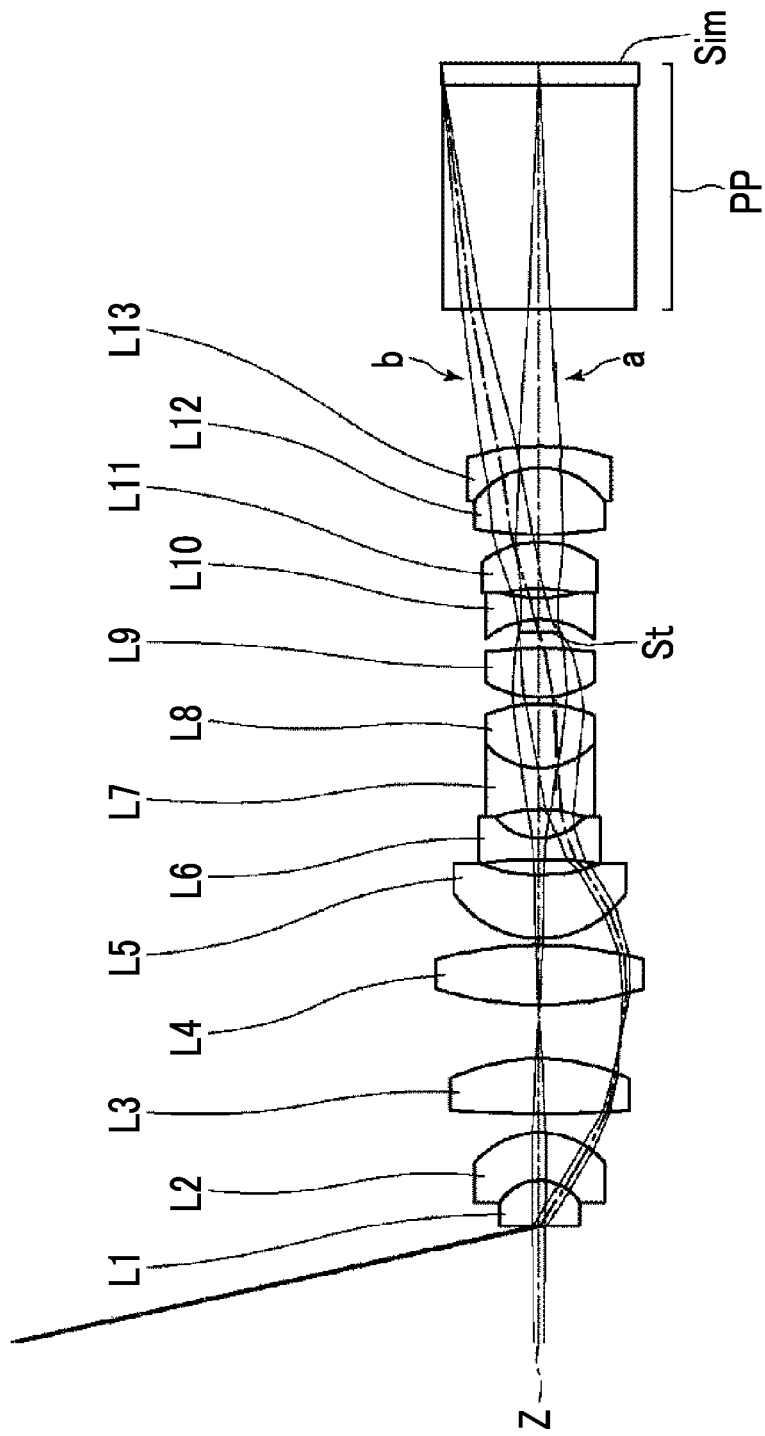
FIG. 3 is a cross-sectional view showing the structure of an objective optical system for an endoscope of Example 3 of the invention.
Figure 11:
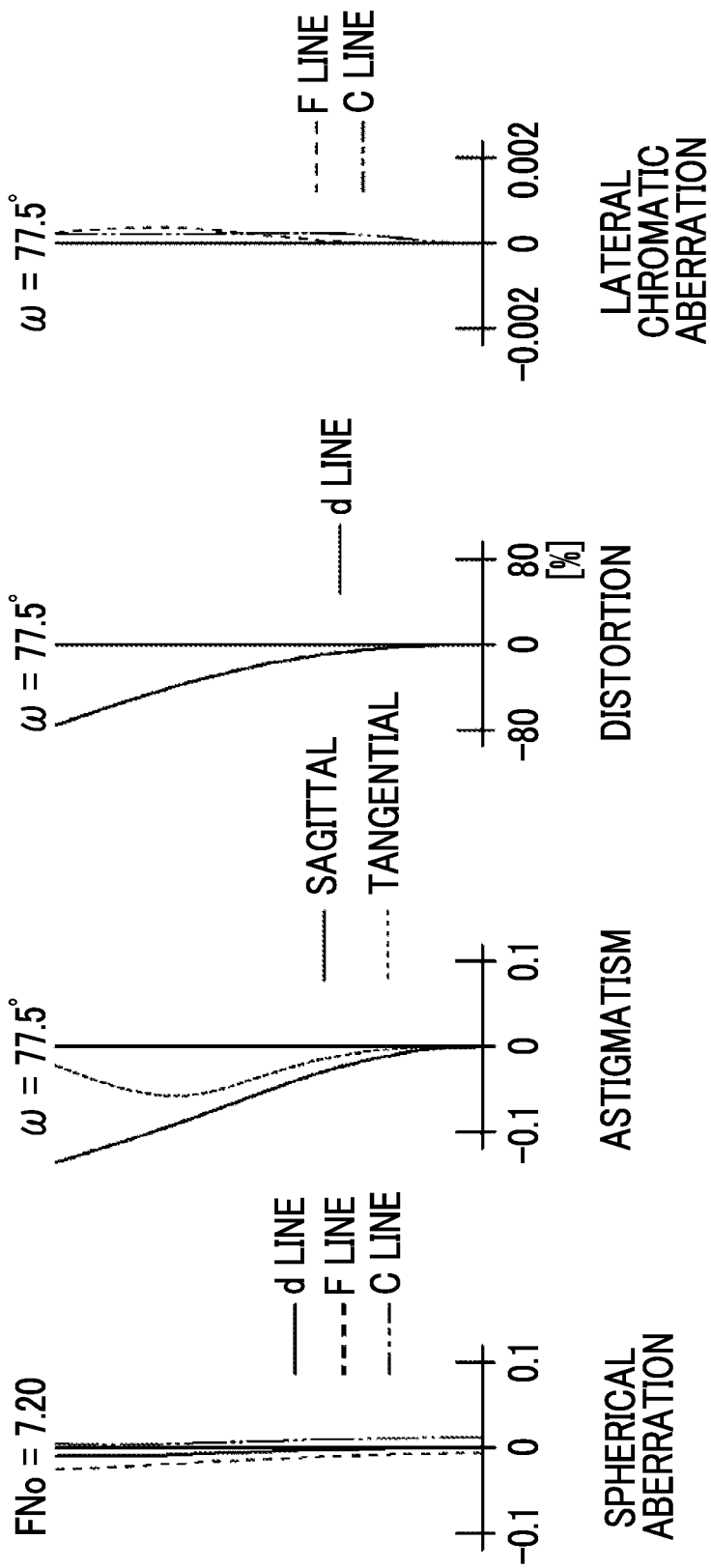
FIG. 11 is a diagram showing the respective aberrations of the objective optical system for an endoscope of Example 3 of the invention.

Next, an objective optical system for an endoscope of Example 3 will be described. FIG. 3 is a cross-sectional view showing the structure of the objective optical system for an endoscope of Example 3. The objective optical system for an endoscope of Example 3 includes 13 lenses, that is, lenses L1 to L13 in this order from an object, and has a structure in which an aperture stop St is disposed in the objective optical system for an endoscope. Further, the lens data of the objective optical system for an endoscope of Example 3 is shown in Table 3, and diagrams showing the respective aberrations are shown in FIG. 11.

TABLE 3

Example 3•LENS DATA (n, ν ARE d LINE)

| Surface Number | Curvature Radius | Surface Spacing | n | ν | Effective Luminous Flux Diameter |
|---|---|---|---|---|---|
| Object Surface | ∞ | 8.120 | | | |
| 1 | ∞ | 0.528 | 1.90043 | 37.4 | 0.179 |
| 2 | −0.524 | 0.545 | 1.89286 | 20.4 | |
| 3 | −0.953 | 0.218 | | | |
| 4 | 15.047 | 0.608 | 1.77250 | 49.6 | |
| 5 | −2.404 | 0.615 | | | |
| 6 | 3.825 | 0.673 | 1.91082 | 35.3 | 2.045 |
| 7 | −4.485 | 0.081 | | | |
| 8 | 1.176 | 0.718 | 2.00100 | 29.1 | |
| 9 | 1.757 | 0.178 | | | |
| 10 | −5.833 | 0.244 | 1.89286 | 20.4 | |
| 11 | 0.642 | 0.324 | | | |
| 12 | −1.551 | 0.475 | 1.89286 | 20.4 | |
| 13 | 0.829 | 0.722 | 1.90043 | 37.4 | |
| 14 | −1.587 | 0.081 | | | |
| 15 | 1.193 | 0.553 | 1.89286 | 20.4 | |
| 16 | −4.597 | 0.184 | | | |
| 17(St) | ∞ | 0.148 | | | |
| 18 | −0.955 | 0.244 | 1.84666 | 23.8 | |
| 19 | 1.671 | 0.108 | | | |
| 20 | −1.689 | 0.534 | 1.85150 | 40.8 | |

TABLE 3-continued

Example 3•LENS DATA (n, v ARE d LINE)

| Surface Number | Curvature Radius | Surface Spacing | n | v | Effective Luminous Flux Diameter |
|---|---|---|---|---|---|
| 21 | −1.029 | 0.081 | | | |
| 22 | 4.851 | 0.759 | 1.61800 | 63.3 | |
| 23 | −0.891 | 0.244 | 1.89286 | 20.4 | |
| 24 | −2.532 | 1.552 | | | |
| 25 | ∞ | 2.558 | 1.55920 | 53.9 | |
| 26 | ∞ | 0.244 | 1.51633 | 64.1 | |
| Imaging Plane | ∞ | | | | |

HI = 1.115

Figure 4:
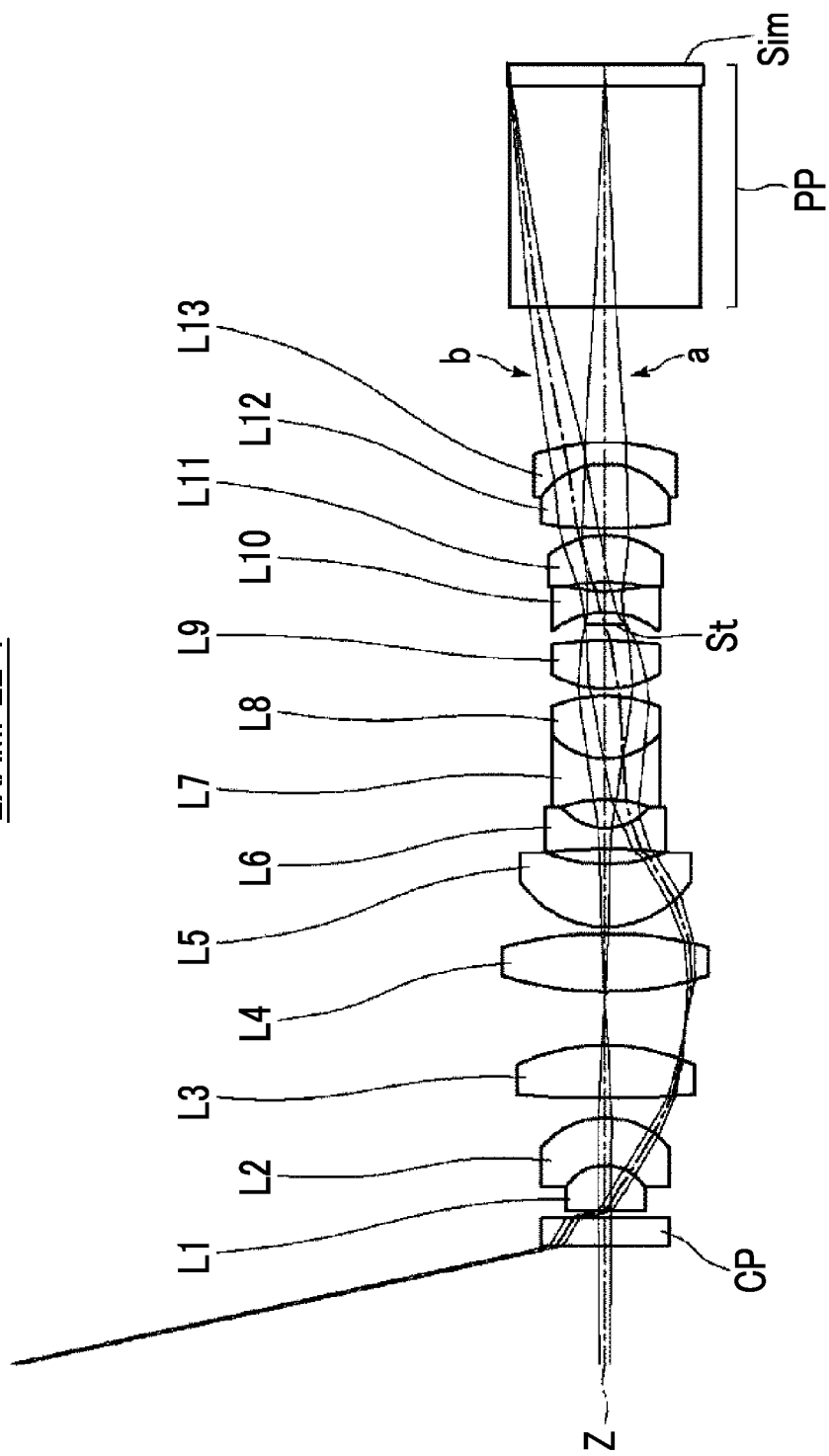
FIG. 4 is a cross-sectional view showing the structure of an objective optical system for an endoscope of Example 4 of the invention.
Figure 12:
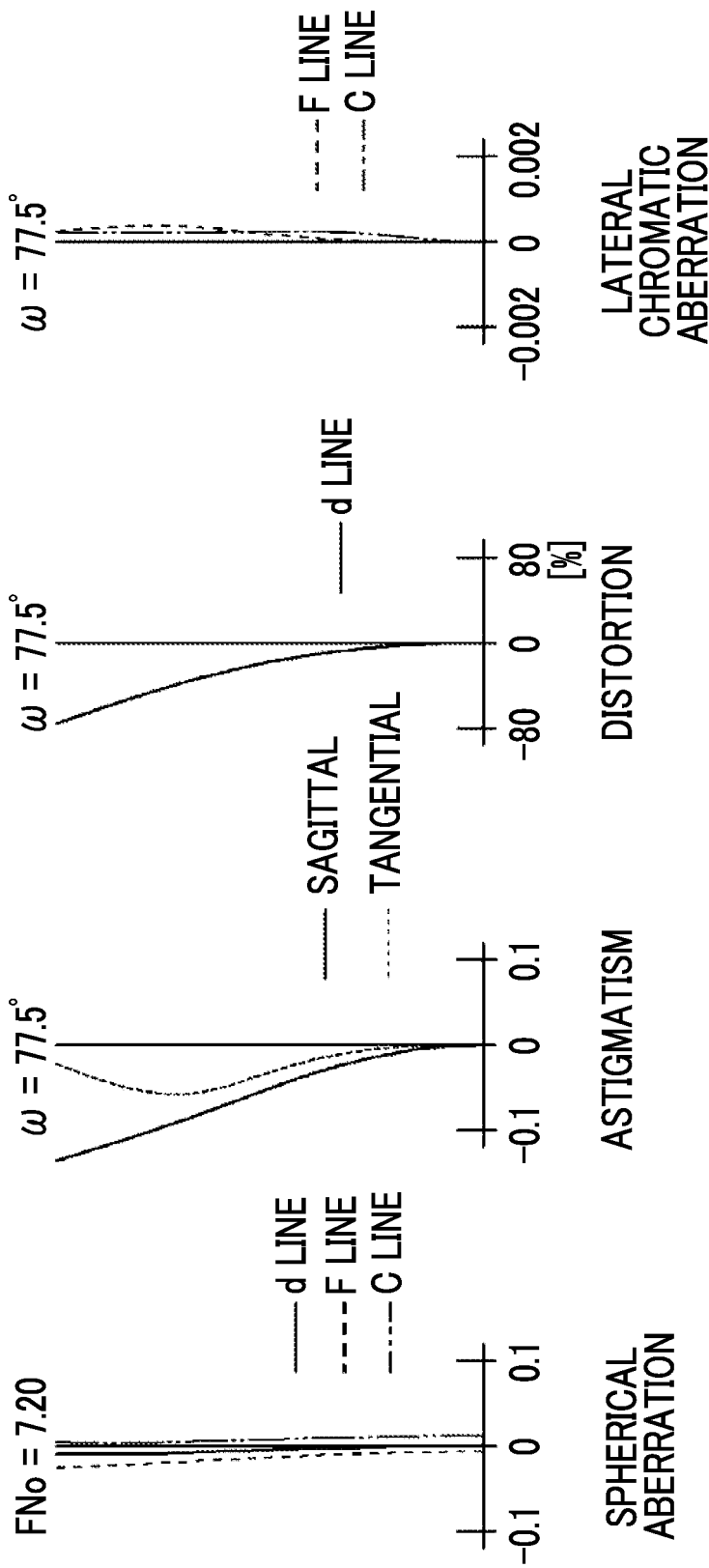
FIG. 12 is a diagram showing the respective aberrations of the objective optical system for an endoscope of Example 4 of the invention.

Next, an objective optical system for an endoscope of Example 4 will be described. FIG. 4 is a cross-sectional view showing the structure of the objective optical system for an endoscope of Example 4. The objective optical system for an endoscope of Example 4 includes a plane-parallel plate CP and 13 lenses, that is, lenses L1 to L13 in this order from an object, and has a structure in which an aperture stop St is disposed in the objective optical system for an endoscope. Further, the lens data of the objective optical system for an endoscope of Example 4 is shown in Table 4, and diagrams showing the respective aberrations of the objective optical system for an endoscope of Example 4 are shown in FIG. 12.

TABLE 4

Example 4•LENS DATA (n, v ARE d LINE)

| Surface Number | Curvature Radius | Surface Spacing | n | v | Effective Luminous Flux Diameter |
|---|---|---|---|---|---|
| Object Surface | ∞ | 8.120 | | | |
| 1 | ∞ | 0.325 | 1.88299 | 40.8 | |
| 2 | ∞ | 0.081 | | | |
| 3 | ∞ | 0.528 | 1.90043 | 37.4 | 0.179 |
| 4 | −0.524 | 0.545 | 1.89286 | 20.4 | |
| 5 | −0.953 | 0.218 | | | |
| 6 | 15.047 | 0.608 | 1.77250 | 49.6 | |
| 7 | −2.404 | 0.615 | | | |
| 8 | 3.825 | 0.673 | 1.91082 | 35.3 | 2.045 |
| 9 | −4.485 | 0.081 | | | |
| 10 | 1.176 | 0.718 | 2.00100 | 29.1 | |
| 11 | 1.757 | 0.178 | | | |
| 12 | −5.833 | 0.244 | 1.89286 | 20.4 | |
| 13 | 0.642 | 0.324 | | | |
| 14 | −1.551 | 0.475 | 1.89286 | 20.4 | |
| 15 | 0.829 | 0.722 | 1.90043 | 37.4 | |
| 16 | −1.587 | 0.081 | | | |
| 17 | 1.193 | 0.553 | 1.89286 | 20.4 | |
| 18 | −4.597 | 0.184 | | | |
| 19(St) | ∞ | 0.148 | | | |
| 20 | −0.955 | 0.244 | 1.84666 | 23.8 | |
| 21 | 1.671 | 0.108 | | | |
| 22 | −1.689 | 0.534 | 1.85150 | 40.8 | |
| 23 | −1.029 | 0.081 | | | |
| 24 | 4.851 | 0.759 | 1.61800 | 63.3 | |
| 25 | −0.891 | 0.244 | 1.89286 | 20.4 | |
| 26 | −2.532 | 1.552 | | | |
| 27 | ∞ | 2.558 | 1.55920 | 53.9 | |
| 28 | ∞ | 0.244 | 1.51633 | 64.1 | |
| Imaging Plane | ∞ | | | | |

HI = 1.115

Figure 5:
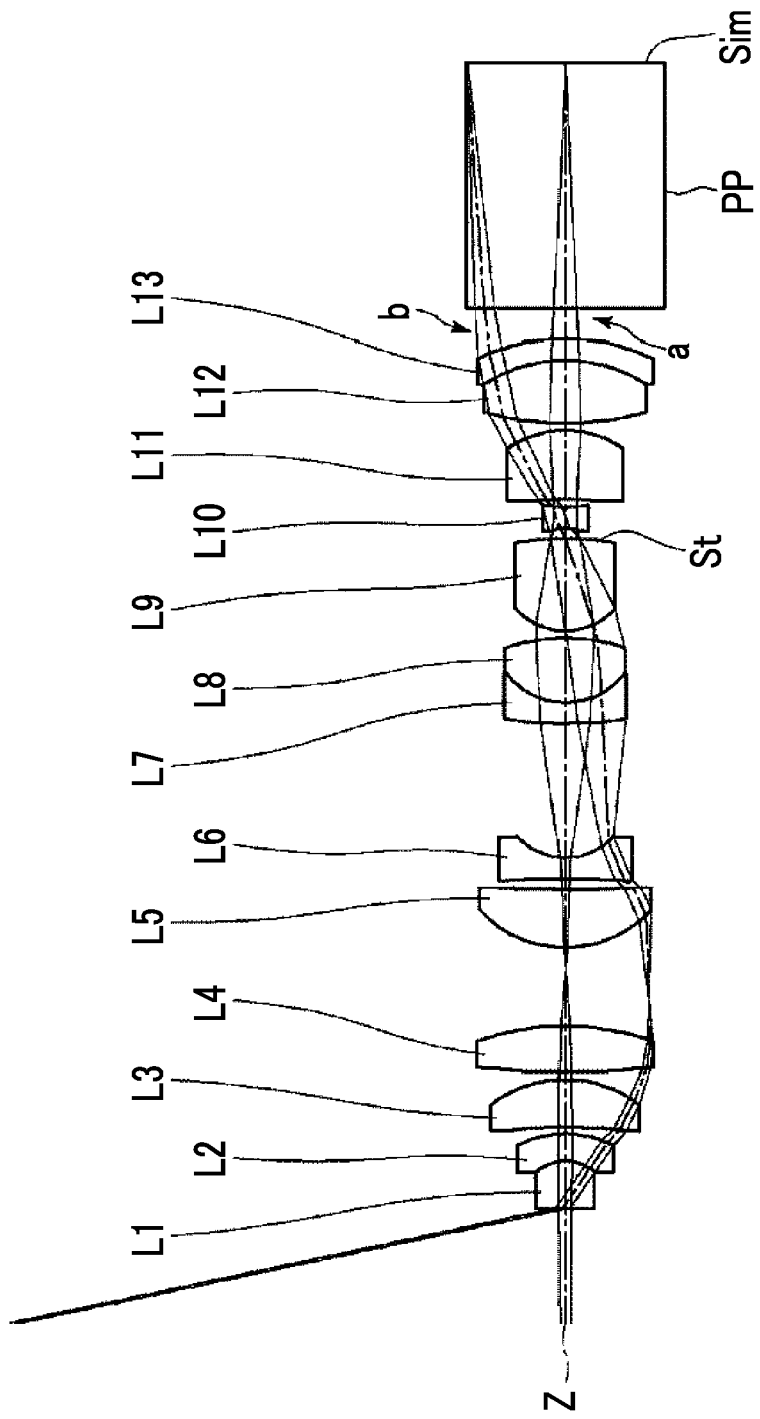
FIG. 5 is a cross-sectional view showing the structure of an objective optical system for an endoscope of Example 5 of the invention.
Figure 13:
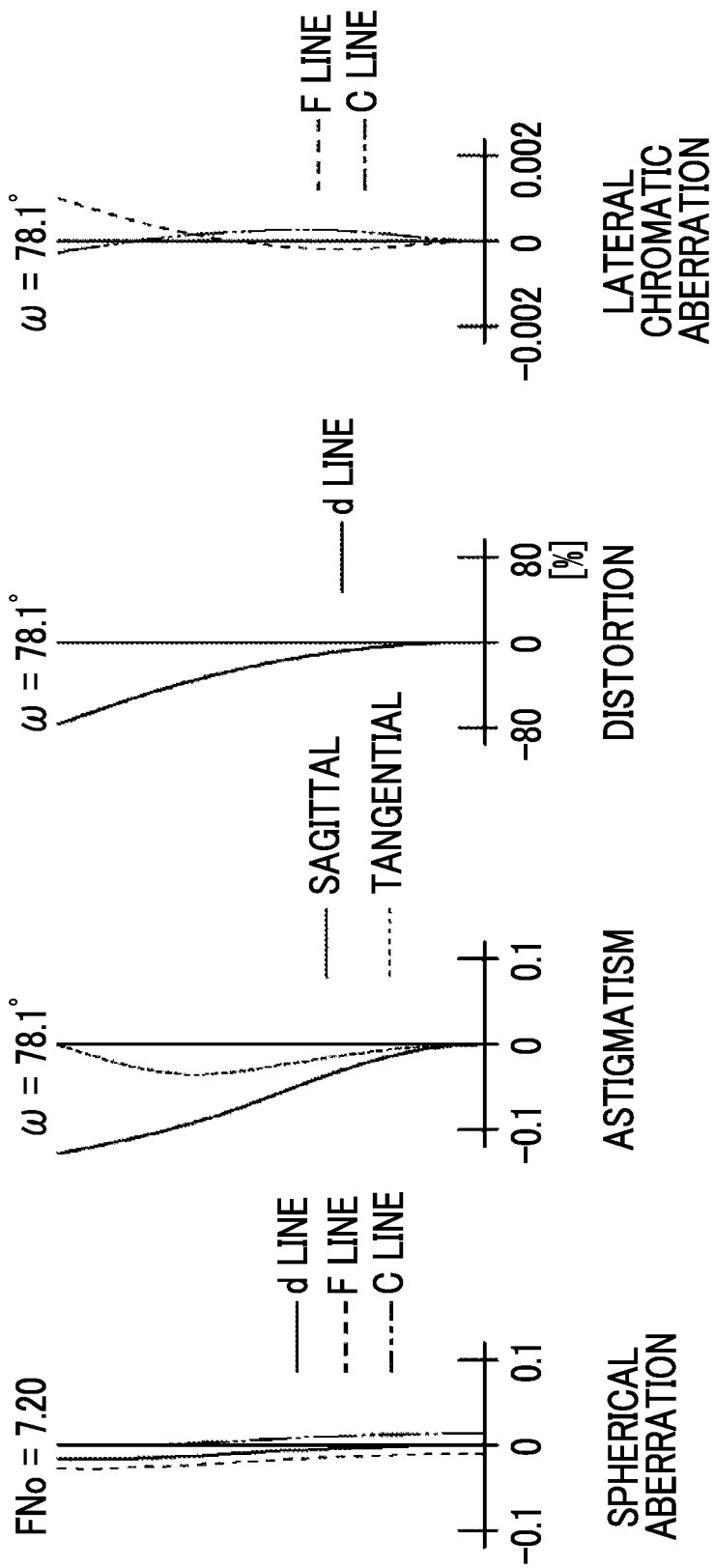
FIG. 13 is a diagram showing the respective aberrations of the objective optical system for an endoscope of Example 5 of the invention.

Next, an objective optical system for an endoscope of Example 5 will be described. FIG. 5 is a cross-sectional view showing the structure of the objective optical system for an endoscope of Example 5. The objective optical system for an endoscope of Example 5 includes 13 lenses, that is, lenses L1 to L13 in this order from an object, and has a structure in which an aperture stop St is disposed in the objective optical system for an endoscope. Further, the lens data of the objective optical system for an endoscope of Example 5 is shown in Table 5, and diagrams showing the respective aberrations of the objective optical system for an endoscope of Example 5 are shown in FIG. 13.

TABLE 5

Example 5•LENS DATA (n, v ARE d LINE)

| Surface Number | Curvature Radius | Surface Spacing | n | v | Effective Luminous Flux Diameter |
|---|---|---|---|---|---|
| Object Surface | ∞ | 8.110 | | | |
| 1 | ∞ | 0.535 | 1.72916 | 54.7 | 0.224 |
| 2 | −0.489 | 0.314 | 1.89286 | 20.4 | |
| 3 | −1.137 | 0.081 | | | |
| 4 | −4.707 | 0.531 | 1.77250 | 49.6 | |
| 5 | −1.382 | 0.081 | | | |
| 6 | 9.424 | 0.519 | 1.89190 | 37.1 | |
| 7 | −2.946 | 0.892 | | | 1.995 |
| 8 | 1.308 | 0.661 | 2.00100 | 29.1 | |
| 9 | 14.334 | 0.121 | | | |
| 10 | −13.335 | 0.243 | 1.89286 | 20.4 | |
| 11 | 0.733 | 1.522 | | | |
| 12 | 3.746 | 0.243 | 1.78470 | 26.3 | |
| 13 | 0.836 | 0.734 | 1.73800 | 32.3 | |
| 14 | −2.071 | 0.081 | | | |
| 15 | 0.738 | 1.050 | 1.48749 | 70.2 | |
| 16 | −3.192 | 0.000 | | | |
| 17(St) | ∞ | 0.118 | | | |
| 18 | −0.537 | 0.243 | 1.84666 | 23.8 | |
| 19 | 1.222 | 0.091 | | | |
| 20 | −1.755 | 0.793 | 1.62041 | 60.3 | |
| 21 | −1.134 | 0.081 | | | |
| 22 | 3.343 | 0.714 | 1.59522 | 67.7 | |
| 23 | −1.692 | 0.243 | 1.89286 | 20.4 | |
| 24 | −2.310 | 0.336 | | | |
| 25 | ∞ | 2.799 | 1.55920 | 53.9 | |
| Imaging Plane | ∞ | | | | |

HI = 1.114

Figure 6:
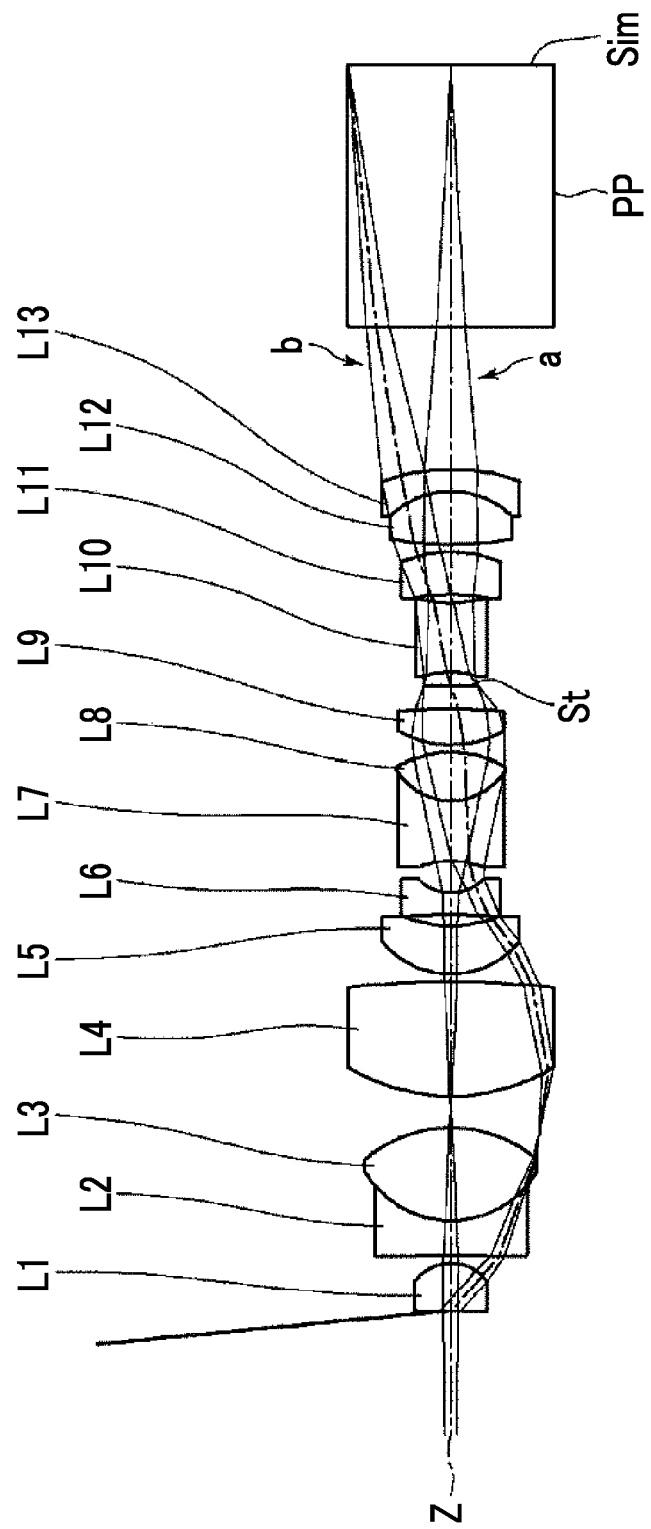
FIG. 6 is a cross-sectional view showing the structure of an objective optical system for an endoscope of Example 6 of the invention.
Figure 14:
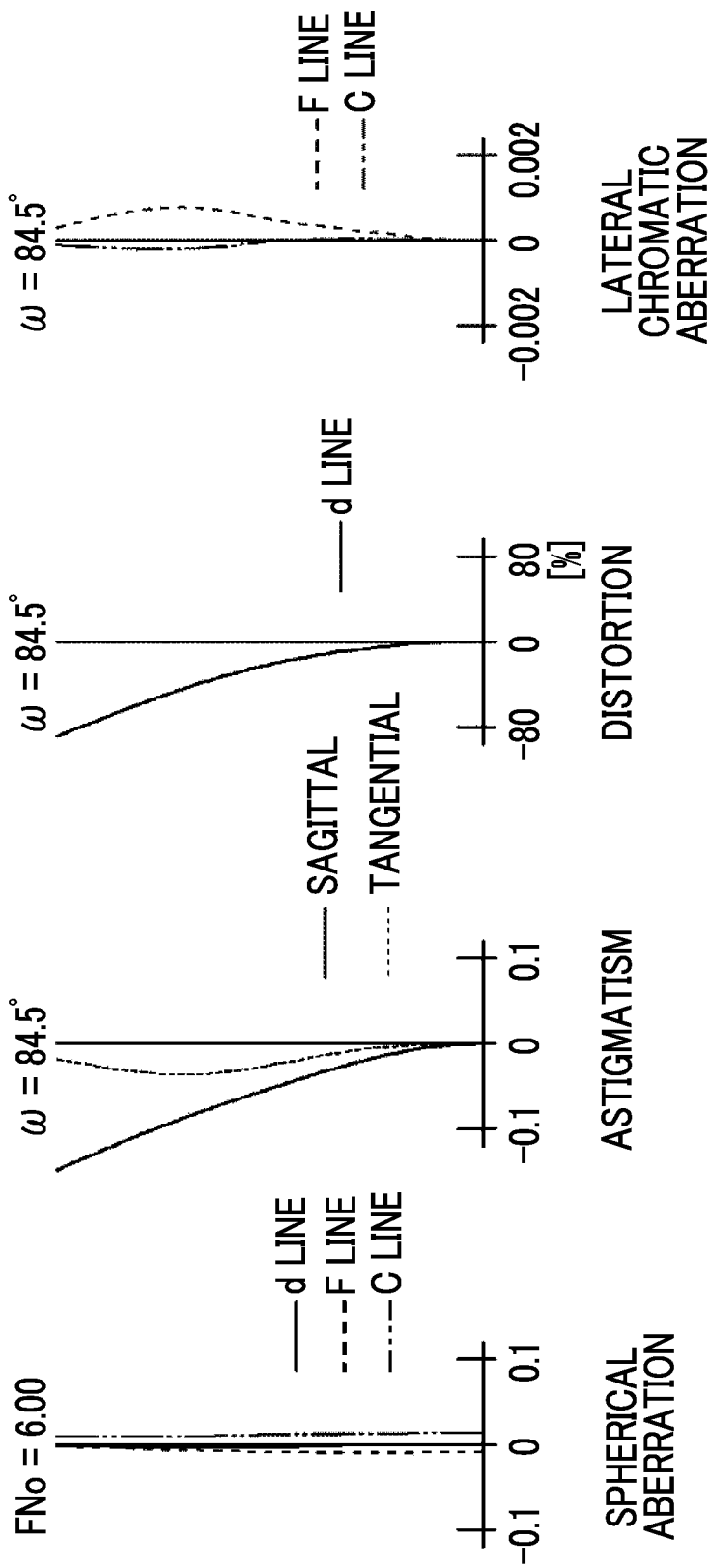
FIG. 14 is a diagram showing the respective aberrations of the objective optical system for an endoscope of Example 6 of the invention.

Next, an objective optical system for an endoscope of Example 6 will be described. FIG. 6 is a cross-sectional view showing the structure of the objective optical system for an endoscope of Example 6. The objective optical system for an endoscope of Example 6 includes 13 lenses, that is, lenses L1 to L13 in this order from an object, and has a structure in which an aperture stop St is disposed in the objective optical system for an endoscope. Further, the lens data of the objective optical system for an endoscope of Example 6 is shown in Table 6, and diagrams showing the respective aberrations of the objective optical system for an endoscope of Example 6 are shown in FIG. 14.

TABLE 6

Example 6•LENS DATA (n, v ARE d LINE)

| Surface Number | Curvature Radius | Surface Spacing | n | v | Effective Luminous Flux Diameter |
|---|---|---|---|---|---|
| Object Surface | ∞ | 8.490 | | | |
| 1 | ∞ | 0.552 | 1.51680 | 64.2 | 0.233 |
| 2 | −0.515 | 0.085 | | | |
| 3 | −126.275 | 0.400 | 1.89286 | 20.4 | |
| 4 | 1.132 | 1.053 | 1.84666 | 23.8 | |
| 5 | −1.511 | 0.362 | | | |
| 6 | 2.252 | 1.299 | 1.89190 | 37.1 | 2.327 |
| 7 | −10.277 | 0.085 | | | |
| 8 | 1.011 | 0.551 | 2.00100 | 29.1 | |

TABLE 6-continued

Example 6•LENS DATA (n, ν ARE d LINE)

| Surface Number | Curvature Radius | Surface Spacing | n | ν | Effective Luminous Flux Diameter |
|---|---|---|---|---|---|
| 9 | 1.499 | 0.118 | | | |
| 10 | −9.557 | 0.255 | 1.89286 | 20.4 | |
| 11 | 0.511 | 0.365 | | | |
| 12 | −0.972 | 0.682 | 1.85896 | 22.7 | |
| 13 | 0.723 | 0.536 | 1.85150 | 40.8 | |
| 14 | −1.317 | 0.085 | | | |
| 15 | 1.190 | 0.415 | 1.89286 | 20.4 | |
| 16 | −5.203 | 0.260 | | | |
| 17(St) | ∞ | 0.150 | | | |
| 18 | −1.014 | 0.789 | 1.89286 | 20.4 | |
| 19 | 1.478 | 0.096 | | | |
| 20 | −2.330 | 0.485 | 1.83481 | 42.7 | |
| 21 | −1.402 | 0.085 | | | |
| 22 | 3.931 | 0.601 | 1.59522 | 67.7 | |
| 23 | −0.999 | 0.255 | 1.78472 | 25.7 | |
| 24 | −2.235 | 1.622 | | | |
| 25 | ∞ | 2.971 | 1.51633 | 64.1 | |
| Imaging Plane | ∞ | | | | |

HI = 1.165

Figure 7:
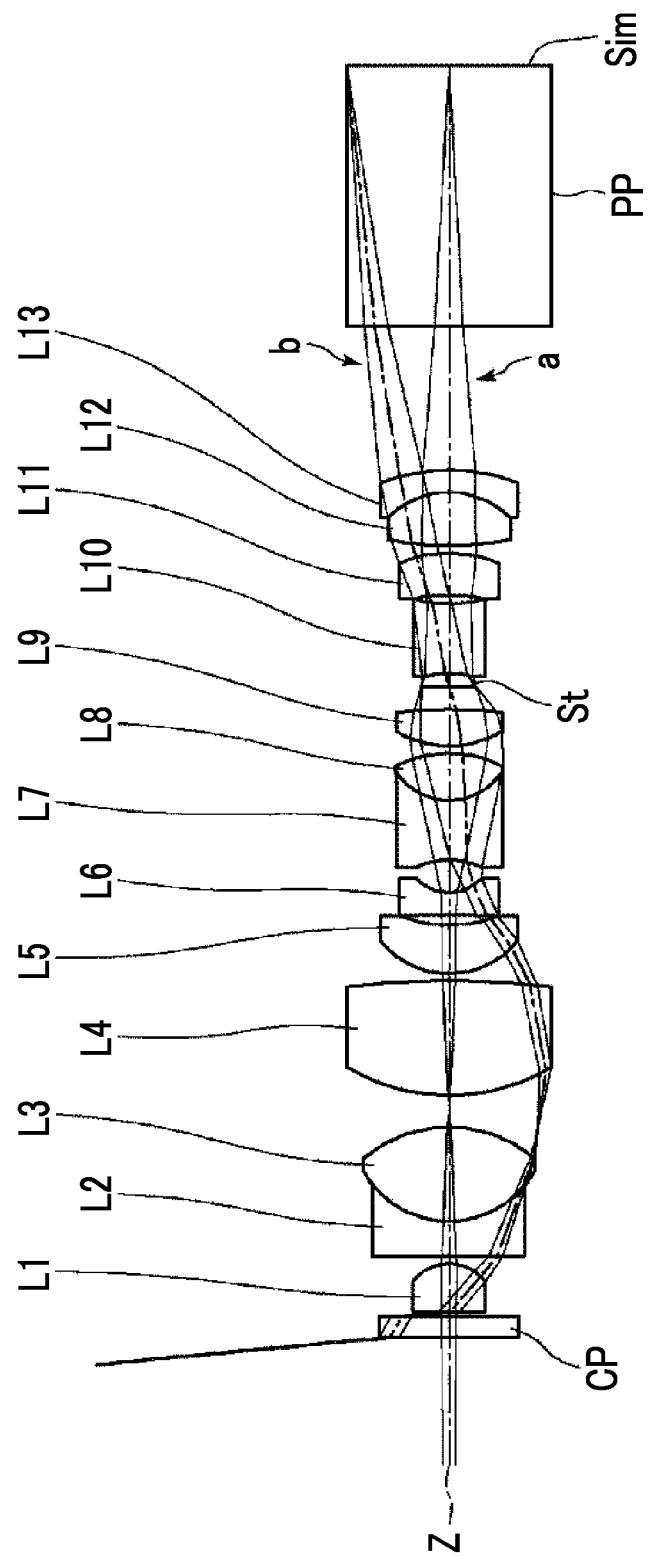
FIG. 7 is a cross-sectional view showing the structure of an objective optical system for an endoscope of Example 7 of the invention.
Figure 15:
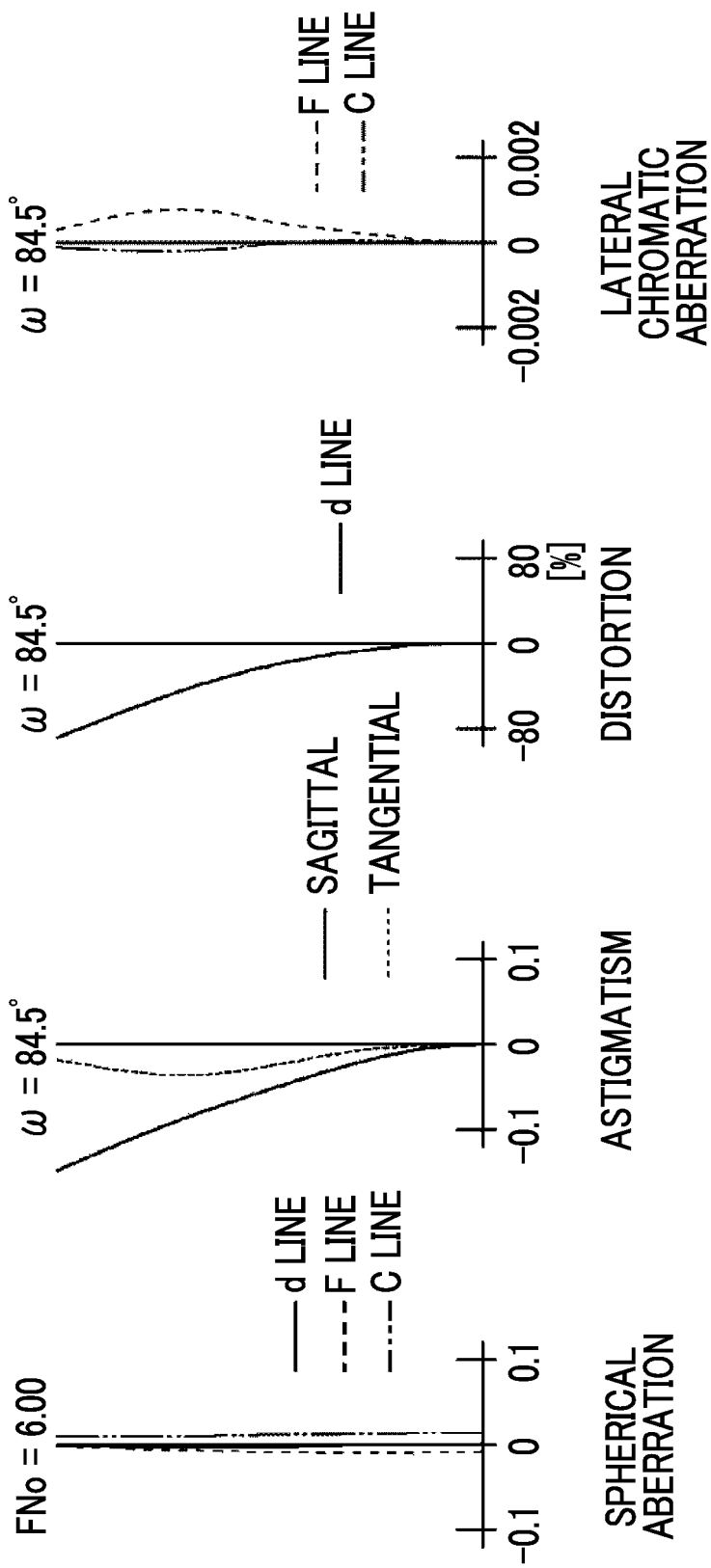
FIG. 15 is a diagram showing the respective aberrations of the objective optical system for an endoscope of Example 7 of the invention.

Next, an objective optical system for an endoscope of Example 7 will be described. FIG. 7 is a cross-sectional view showing the structure of an objective optical system for an endoscope of Example 7. The objective optical system for an endoscope of Example 7 includes a plane-parallel plate CP and 13 lenses, that is, lenses L1 to L13 in this order from an object, and has a structure in which an aperture stop St is disposed in the objective optical system for an endoscope. Further, the lens data of the objective optical system for an endoscope of Example 7 is shown in Table 7, and diagrams showing the respective aberrations of the objective optical system for an endoscope of Example 7 are shown in FIG. 15.

TABLE 7

Example 7•LENS DATA (n, ν ARE d LINE)

| Surface Number | Curvature Radius | Surface Spacing | n | ν | Effective Luminous Flux Diameter |
|---|---|---|---|---|---|
| Object Surface | ∞ | 8.490 | | | |
| 1 | ∞ | 0.250 | 2.00100 | 29.1 | |
| 2 | ∞ | 0.050 | | | |
| 3 | ∞ | 0.552 | 1.51680 | 64.2 | 0.233 |
| 4 | −0.515 | 0.085 | | | |
| 5 | −126.275 | 0.400 | 1.89286 | 20.4 | |
| 6 | 1.132 | 1.053 | 1.84666 | 23.8 | |
| 7 | −1.511 | 0.362 | | | |
| 8 | 2.252 | 1.299 | 1.89190 | 37.1 | 2.327 |
| 9 | −10.277 | 0.085 | | | |
| 10 | 1.011 | 0.551 | 2.00100 | 29.1 | |
| 11 | 1.499 | 0.118 | | | |
| 12 | −9.557 | 0.255 | 1.89286 | 20.4 | |
| 13 | 0.511 | 0.365 | | | |
| 14 | −0.972 | 0.682 | 1.85896 | 22.7 | |
| 15 | 0.723 | 0.536 | 1.85150 | 40.8 | |
| 16 | −1.317 | 0.085 | | | |
| 17 | 1.190 | 0.415 | 1.89286 | 20.4 | |
| 18 | −5.203 | 0.260 | | | |
| 19(St) | ∞ | 0.150 | | | |
| 20 | −1.014 | 0.789 | 1.89286 | 20.4 | |
| 21 | 1.478 | 0.096 | | | |
| 22 | −2.330 | 0.485 | 1.83481 | 42.7 | |
| 23 | −1.402 | 0.085 | | | |
| 24 | 3.931 | 0.601 | 1.59522 | 67.7 | |

TABLE 7-continued

Example 7•LENS DATA (n, ν ARE d LINE)

| Surface Number | Curvature Radius | Surface Spacing | n | ν | Effective Luminous Flux Diameter |
|---|---|---|---|---|---|
| 25 | −0.999 | 0.255 | 1.78472 | 25.7 | |
| 26 | −2.235 | 1.622 | | | |
| 27 | ∞ | 2.971 | 1.51633 | 64.1 | |
| Imaging Plane | ∞ | | | | |

HI = 1.165

Figure 8:
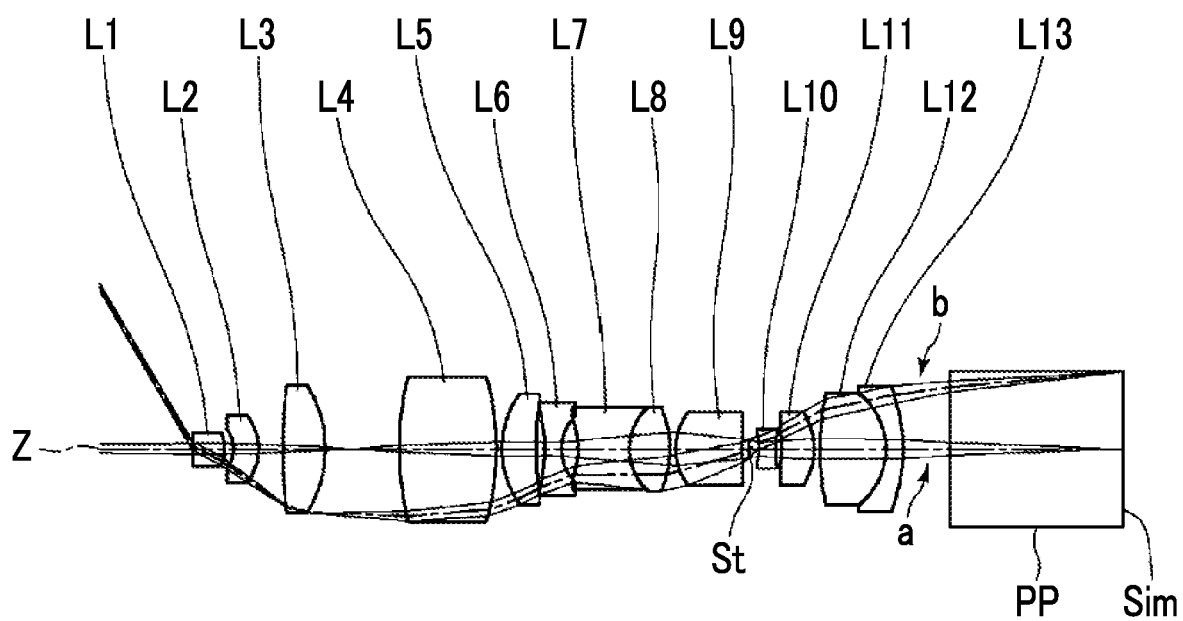
FIG. 8 is a cross-sectional view showing the structure of an objective optical system for an endoscope of Example 8 of the invention.
Figure 16:
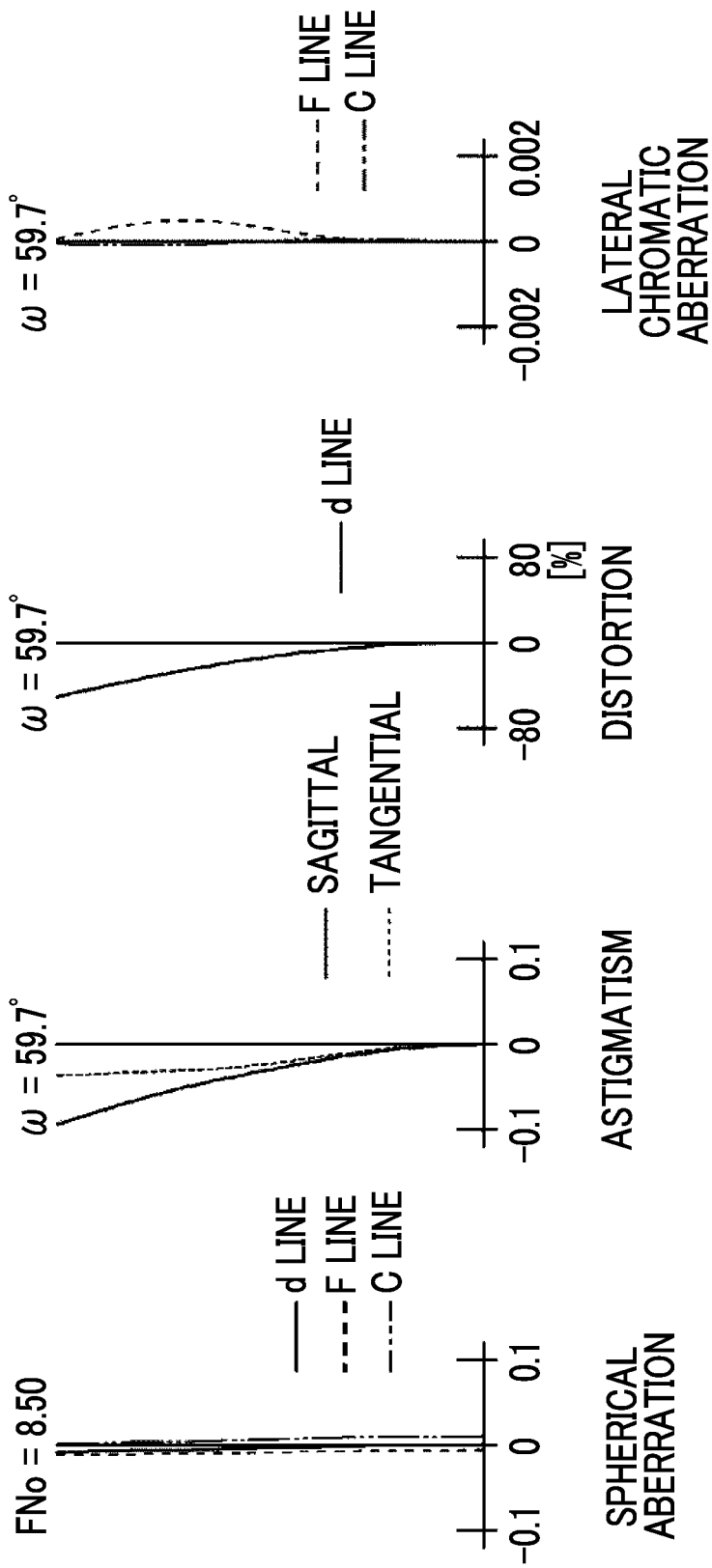
FIG. 16 is a diagram showing the respective aberrations of the objective optical system for an endoscope of Example 8 of the invention.

Next, an objective optical system for an endoscope of Example 8 will be described. FIG. 8 is a cross-sectional view showing the structure of an objective optical system for an endoscope of Example 8. The objective optical system for an endoscope of Example 8 includes 13 lenses, that is, lenses L1 to L13 in this order from an object, and has a structure in which an aperture stop St is disposed in the objective optical system for an endoscope. Further, the lens data of the objective optical system for an endoscope of Example 8 is shown in Table 8, and diagrams showing the respective aberrations of the objective optical system for an endoscope of Example 8 are shown in FIG. 16.

TABLE 8

Example 8•LENS DATA (n, ν ARE d LINE)

| Surface Number | Curvature Radius | Surface Spacing | n | ν | Effective Luminous Flux Diameter |
|---|---|---|---|---|---|
| Object Surface | ∞ | 6.370 | | | |
| 1 | ∞ | 0.373 | 1.95375 | 32.3 | 0.156 |
| 2 | −0.558 | 0.102 | | | |
| 3 | −0.384 | 0.284 | 1.80518 | 25.4 | |
| 4 | −0.638 | 0.283 | | | |
| 5 | 6.354 | 0.480 | 1.77250 | 49.6 | |
| 6 | −1.359 | 0.835 | | | |
| 7 | 3.334 | 1.103 | 1.80518 | 25.4 | 1.647 |
| 8 | −3.062 | 0.064 | | | |
| 9 | 1.083 | 0.395 | 1.80518 | 25.4 | |
| 10 | 5.769 | 0.088 | | | |
| 11 | −2.007 | 0.191 | 1.51633 | 64.1 | |
| 12 | 0.533 | 0.187 | | | |
| 13 | −1.067 | 0.574 | 1.76182 | 26.5 | |
| 14 | 0.653 | 0.459 | 1.78800 | 47.4 | |
| 15 | −1.221 | 0.064 | | | |
| 16 | 0.688 | 0.757 | 1.78800 | 47.4 | |
| 17 | 1.820 | 0.072 | | | |
| 18(St) | ∞ | 0.120 | | | |
| 19 | −0.396 | 0.191 | 1.80518 | 25.4 | |
| 20 | 1.861 | 0.064 | | | |
| 21 | −2.100 | 0.370 | 1.62041 | 60.3 | |
| 22 | −0.778 | 0.064 | | | |
| 23 | 2.787 | 0.750 | 1.76200 | 40.1 | |
| 24 | −0.810 | 0.191 | 1.78800 | 47.4 | |
| 25 | −2.108 | 0.533 | | | |
| 26 | ∞ | 1.975 | 1.55920 | 53.9 | |
| Imaging Plane | ∞ | | | | |

HI = 0.8747

Values corresponding to Conditional expressions (1) to (4) of the objective optical systems for an endoscope of Examples 1 to 8 are shown in Table 9. A d line is also used as a reference wavelength in all examples, and the values shown in Table 9 are values that are obtained in a case in which this reference wavelength is used.

TABLE 9

| Expression Number | Conditional Expression | Example 1 | Example 2 | Example 3 | Example 4 |
|---|---|---|---|---|---|
| (1) | \|FS/f\| | 0.257 | 0.257 | 0.027 | 0.027 |
| (2) | βR | −1.36 | −1.36 | −1.14 | −1.14 |
| (3) | BD/(2 × HI) | 0.84 | 0.84 | 0.92 | 0.92 |
| (4) | HI/(tan(ω) × \|f\|) | 0.57 | 0.57 | 0.25 | 0.25 |

| Expression Number | Conditional Expression | Example 5 | Example 6 | Example 7 | Example 8 |
|---|---|---|---|---|---|
| (1) | \|FS/f\| | 0.055 | 0.008 | 0.008 | 0.032 |
| (2) | βR | −1.13 | −1.06 | −1.06 | −1.26 |
| (3) | BD/(2 × HI) | 0.90 | 1.00 | 1.00 | 0.94 |
| (4) | HI/(tan(ω) × \|f\|) | 0.23 | 0.11 | 0.11 | 0.51 |

It is found from the above-mentioned data that all the objective optical systems for an endoscope of Examples 1 to 8 satisfy Conditional expressions (1) to (4), have wide total angles of view of 90° or more, have small effective luminous flux diameters on lens surfaces closest to the object, and have good optical performance.

Figure 17:
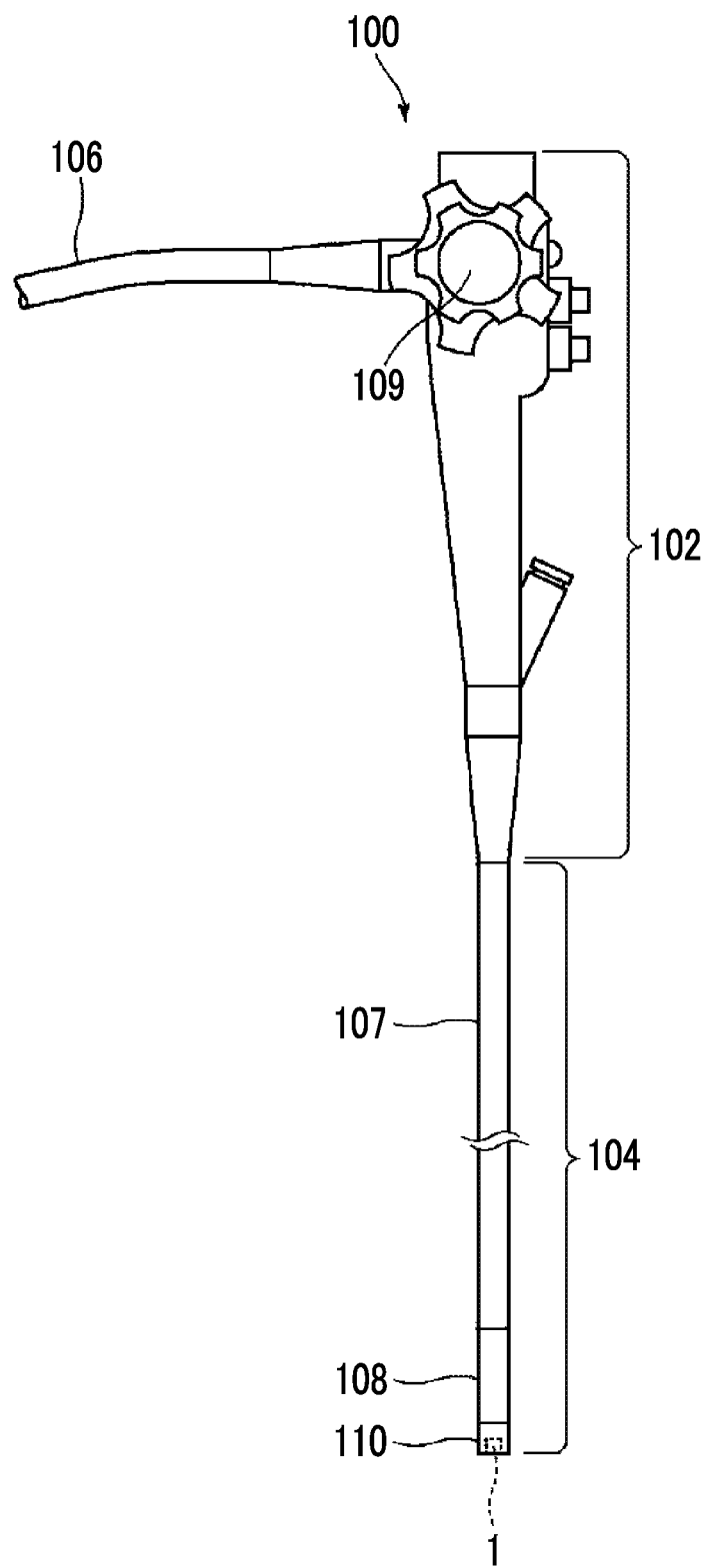
FIG. 17 is a diagram showing a schematic structure of an endoscope according to an embodiment of the invention.
Figure 18:
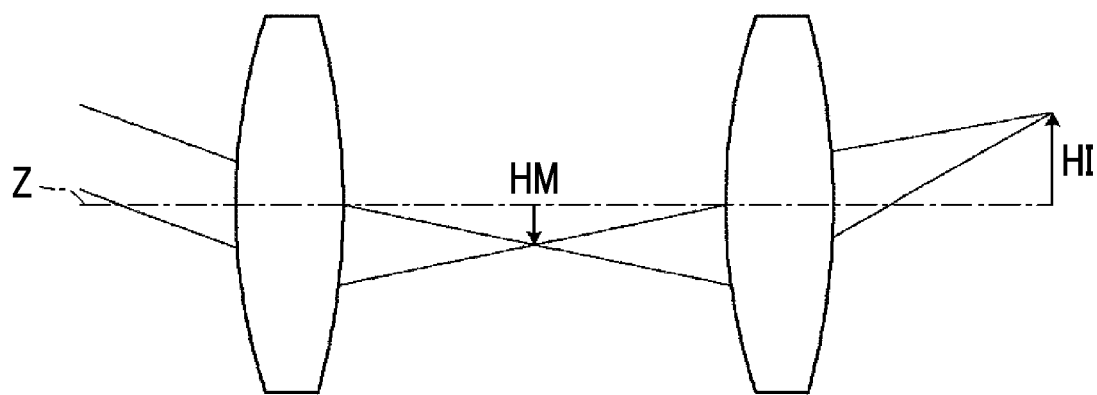
FIG. 18 is a diagram illustrating a relay magnification.

Next, an embodiment of an endoscope to which the objective optical system for an endoscope of the invention is applied will be described with reference to FIG. 17. FIG. 17 is a diagram showing the schematic structure of the entire endoscope. The endoscope 100 shown in FIG. 17 mainly includes an operation unit 102, an insertion part 104, and a universal cord 106 that is connected to a connector part (not shown). A large portion of the insertion part 104 is a soft portion 107 that is bendable in any direction along an insertion path, a bendable portion 108 is connected to the distal end of the soft portion 107, and a distal end portion 110 is connected to the distal end of the bendable portion 108. The bendable portion 108 is provided to allow the distal end portion 110 to turn in a desired direction, and can be operated to be bent by the rotational movement of a bending operation knob 109 provided on the operation unit 102. An objective optical system 1 for an endoscope according to the embodiment of the invention is provided in the distal end of the distal end portion 110. The objective optical system 1 for an endoscope is schematically shown in FIG. 17. Since the endoscope of this embodiment includes the objective optical system 1 for an endoscope, the distal end portion 110 of the endoscope can be reduced in size and the endoscope has a wide angle and can acquire good images.

The invention has been described using the embodiment and examples, but the invention can have various modifications without being limited to the above-mentioned embodiment and the above-mentioned examples. For example, the curvature radius, the surface spacing, the refractive index, and Abbe's number of each lens may have other values without being limited to the values shown in the above-mentioned examples.

Further, the objective optical system for an endoscope may include an aspherical lens, a GRIN lens, and/or a diffractive optical element other than a spherical lens.

EXPLANATION OF REFERENCES

1: objective optical system for endoscope
100: endoscope
102: operation unit
104: insertion part
106: universal cord
107: soft portion
108: bendable portion
109: bending operation knob
110: distal end portion
CP: plane-parallel plate
L1 to L13: lens
PP: optical member
Sim: imaging plane
St: aperture stop
a: luminous flux on axis
b: luminous flux corresponding to maximum angle of view
Z: optical axis

What is claimed is:

1. An objective optical system for an endoscope that forms an intermediate image at a position conjugate to an object surface and forms the intermediate image on an imaging plane again, comprising:
a stop that is provided between the intermediate image and the imaging plane,
wherein Conditional expression (1) is satisfied in a case in which a distance between a lens surface closest to an object and a paraxial entrance pupil position on an optical axis is denoted by FS and a focal length of the entire system is denoted by f, $$|FS/f|<0.75 \quad (1)$$

and wherein Conditional expression (3) is satisfied in a case in which a maximum effective luminous flux diameter among effective luminous flux diameters on lens surfaces of the entire system is denoted by BD and a maximum effective image height on the imaging plane is denoted by HI, $$BD/(2\times HI)<1.2 \quad (3).$$

2. The objective optical system for an endoscope according to claim 1,
wherein Conditional expression (2) is satisfied in a case in which a paraxial relay magnification of the intermediate image on the imaging plane is denoted by βR, $$-2<\beta R<-0.8 \quad (2).$$

3. The objective optical system for an endoscope according to claim 2,
wherein Conditional expression (2-1) is satisfied, $$-1.5<\beta R<-0.9 \quad (2-1).$$

4. The objective optical system for an endoscope according to claim 1, further comprising:
a plane-parallel plate that is provided to be closer to the object than the lens surface closest to the object.

5. The objective optical system for an endoscope according to claim 1,
wherein Conditional expression (1-1) is satisfied, $$0\leq|FS/f|<0.5 \quad (1-1).$$

6. The objective optical system for an endoscope according to claim 1,
wherein Conditional expression (3-1) is satisfied, $$0.5<BD/(2\times HI)<1.1 \quad (3-1).$$

7. An endoscope comprising:
the objective optical system for an endoscope according to claim 1.

8. An objective optical system for an endoscope that forms an intermediate image at a position conjugate to an object surface and forms the intermediate image on an imaging plane again, comprising:
a stop that is provided between the intermediate image and the imaging plane, wherein Conditional expression (1) is satisfied in a case in which a distance between a lens surface closest to an object and a paraxial entrance pupil position on an optical axis is denoted by FS and a focal length of the entire system is denoted by f, $$|FS/f|<0.75 \qquad (1), \text{ and}$$

wherein Conditional expression (4) is satisfied in a case in which a maximum effective image height on the imaging plane is denoted by HI and a half angle of view of the entire system is denoted by ω, $$HI/(\tan(\omega) \times |f|) < 0.75 \qquad (4).$$

9. The objective optical system for an endoscope according to claim 8,
wherein Conditional expression (4-1) is satisfied, $$0.01 < HI/(\tan(\omega) \times |f|) < 0.65 \qquad (4\text{-}1).$$

10. The objective optical system for an endoscope according to claim 8,
wherein Conditional expression (2) is satisfied in a case in which a paraxial relay magnification of the intermediate image on the imaging plane is denoted by βR, $$-2 < \beta R < -0.8 \qquad (2).$$

11. The objective optical system for an endoscope according to claim 10,
wherein Conditional expression (2-1) is satisfied, $$-1.5 < \beta R < -0.9 \qquad (2\text{-}1).$$

12. The objective optical system for an endoscope according to claim 8, further comprising:
a plane-parallel plate that is provided to be closer to the object than the lens surface closest to the object.

13. The objective optical system for an endoscope according to claim 8,
wherein Conditional expression (1-1) is satisfied, $$0 \le |FS/f| < 0.5 \qquad (1\text{-}1).$$

14. An endoscope comprising:
the objective optical system for an endoscope according to claim 8.

\* \* \* \* \*